United States Patent
Choi

(10) Patent No.: US 8,083,680 B2
(45) Date of Patent: Dec. 27, 2011

(54) ULTRASOUND SYSTEM AND METHOD FOR FORMING AN ULTRASOUND IMAGE

(75) Inventor: Do Young Choi, Seoul (KR)

(73) Assignee: Medison Co., Ltd., Hongchun-gun (KR)

(*) Notice: Subject to any disclaimer, the term of this patent is extended or adjusted under 35 U.S.C. 154(b) by 949 days.

(21) Appl. No.: 12/051,325

(22) Filed: Mar. 19, 2008

(65) Prior Publication Data

US 2008/0234583 A1    Sep. 25, 2008

(30) Foreign Application Priority Data

Mar. 20, 2007   (KR) .................. 10-2007-0026909

(51) Int. Cl.
*A61B 8/00*   (2006.01)

(52) U.S. Cl. ......... 600/443; 600/437; 600/407; 600/463

(58) Field of Classification Search .................. 600/437, 600/407, 443–447; 382/128
See application file for complete search history.

(56) References Cited

U.S. PATENT DOCUMENTS

| | | | |
|---|---|---|---|
| 5,934,288 A | 8/1999 | Avila et al. | |
| 6,370,480 B1* | 4/2002 | Gupta et al. | 702/39 |
| 2002/0151781 A1* | 10/2002 | Ohishi et al. | 600/407 |
| 2005/0101863 A1* | 5/2005 | Kawagishi et al. | 600/443 |
| 2005/0226482 A1 | 10/2005 | Kuduvalli | |
| 2005/0273009 A1* | 12/2005 | Deischinger et al. | 600/437 |
| 2006/0020202 A1* | 1/2006 | Mathew et al. | 600/437 |
| 2006/0250395 A1 | 11/2006 | Kwon et al. | |
| 2007/0236492 A1 | 10/2007 | Ahn et al. | |

FOREIGN PATENT DOCUMENTS

| | | |
|---|---|---|
| EP | 1 419 737 A1 | 5/2004 |
| JP | 2007-54635 | 3/2007 |
| KR | 10-2006-0115595 | 11/2006 |
| KR | 10-2007-0021420 | 2/2007 |

OTHER PUBLICATIONS

Raj Shekhar, et al., "Cine MPR: Interactive Multiplanar Reformatting of Four-Dimensional Cardiac Data Using Hardware-Accelerated Texture Mapping", IEEE Transactions on Information Technology in Biomedicine, XP-011106640, vol. 7, No. 4, Dec. 2003, pp. 384-393.

Office Action issued Sep. 13, 2010, in Korea Patent Application No. 10-2007-0026909.

Notice of Allowance issued on Feb. 28, 2011 in the corresponding Korean Application No. 10-2007-0026909.

\* cited by examiner

*Primary Examiner* — Tse Chen
*Assistant Examiner* — Joel F Brutus
(74) *Attorney, Agent, or Firm* — Oblon, Spivak, McClelland, Maier & Neustadt, L.L.P.

(57) ABSTRACT

The present invention is directed to an ultrasound system and a method for reformatting a planar image. The ultrasound system includes a volume data acquiring unit and an image processing unit. The volume data acquiring unit may acquire volume data by transmitting/receiving ultrasound signals to/from a target object of an un-echoic area. The image processing unit may perform inverse volume rendering upon the volume data to form a 3-dimensional image showing the target object and set a region of interest (ROI) on the target object in response to a user input. The image processor detects data corresponding to the ROI from the volume data and reformats the detected data to form a planar image.

10 Claims, 4 Drawing Sheets

ULTRASOUND SYSTEM AND METHOD FOR FORMING AN ULTRASOUND IMAGE

The present application claims priority from Korean Patent Application No. 10-2007-0026909 filed on Mar. 20, 2007, the entire subject matter of which is incorporated herein by reference.

BACKGROUND OF THE INVENTION

1. Technical Field

The present invention generally relates to ultrasound systems, and more particularly to an ultrasound system and a method for displaying multi-planar images.

2. Background Art

The ultrasound system has become an important and popular diagnostic tool due to its non-invasive and non-destructive nature. Modern high-performance ultrasound imaging diagnostic systems and techniques are commonly used to produce two- or three-dimensional images of internal features of patients.

An ultrasound system generally uses a probe containing an array of piezoelectric elements to transmit and receive ultrasound signals. The ultrasound system forms an image of human internal tissues by electrically exciting transducer elements to generate ultrasound signals that travel into the body. Echoes reflected from tissues and organs return to the transducer element and are converted into electrical signals, which are amplified and processed to produce ultrasound data. The ultrasound data may include volume data obtained by using a 3-dimensional probe, etc.

Generally, the ultrasound system is configured to perform volume rendering upon the volume data to form a 3-dimensional ultrasound image. Also, the ultrasound system may be adapted to reformat planar images by using a reference plane (e.g., sagittal plane, coronal plane or axial plane) or an arbitrary plane set in the volume data, which is referred to as a multi-planar reformatting (MPR) method. The MPR method is widely used in various medical imaging fields in addition to the ultrasound fields.

However, the MPR method is carried out by reformatting the planar images with planes having merely different directions in the volume data in the conventional ultrasound system. Thus, it is difficult to obtain sufficient information regarding a target object to be reformatted to multi-planar images. As such, there is a problem in that the target object, which exists in many planes and has un-echoic areas (e.g., blood vessel), cannot be reformatted.

DETAILED DESCRIPTION OF THE INVENTION

Figure 1:
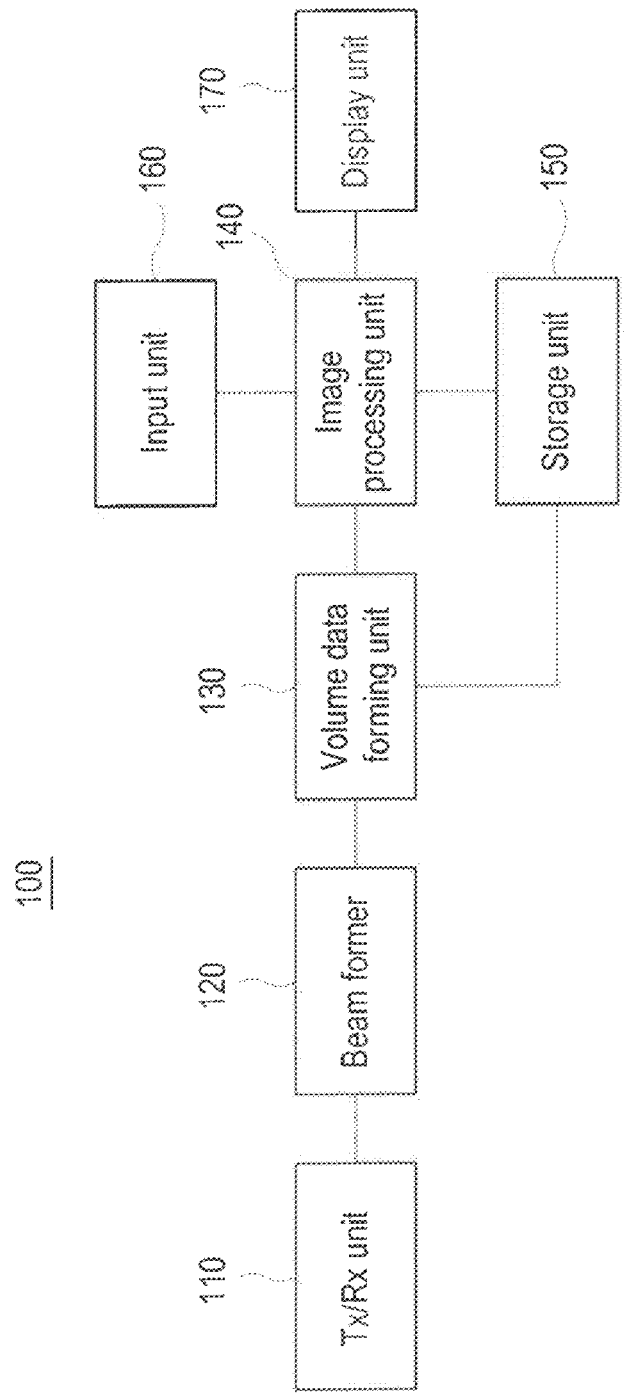
FIG. 1 is a block diagram showing an ultrasound system constructed in accordance with one embodiment of the present invention.

FIG. 1 is a block diagram showing an ultrasound system constructed in accordance with one embodiment of the present invention. Referring to FIG. 1, the ultrasound system 100 includes a Transmit/Receive (T/R) unit 110, a beam former 120, a volume data forming unit 130, an image processing unit 140, a storage unit 150, an input unit 160 and a display unit 170.

The T/R unit 110 may be operable to transmit ultrasound signals to a target object and receive ultrasound echo signals reflected from the target object to form reception signals. The T/R unit 110 may be a probe including a plurality of transducer elements for reciprocally converting ultrasound signals and electrical signals. The ultrasound signals transmitted from the T/R unit 110 may be propagated into the target object along an axial direction.

The beam former 120 may be operable to focus the reception signals by considering a distance between each transducer element and a focal point set in the target object and positions between the transducer elements.

The volume data forming unit 130 may be operable to form volume data based on the focused reception signals. The volume data may include position information corresponding to pixels (or voxels) of a 3-dimensional ultrasound image (i.e., coordinate information at a 3-dimensional coordinate system) and brightness information of the pixels (or voxels). The volume data formed in the volume data forming unit 130 may be stored in the storage unit 150.

Figure 2:
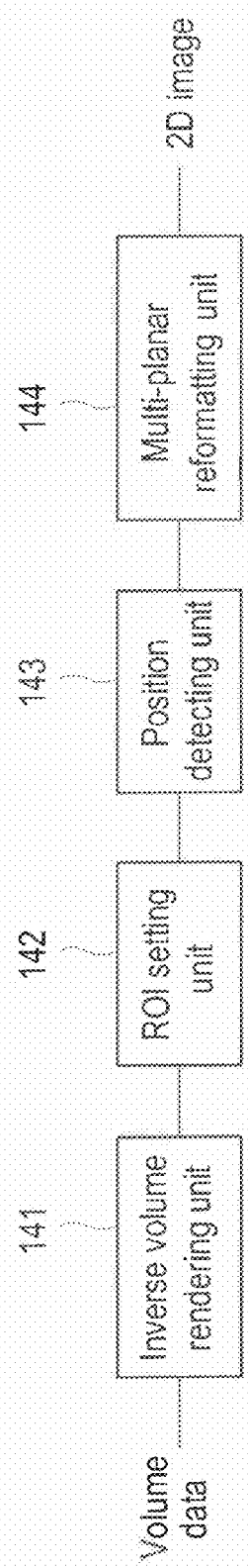
FIG. 2 is a block diagram of an image processing unit constructed in accordance with one embodiment of the present invention.

The image processing unit 140 may be operable to reformat a planar image based on the volume data. As illustrated in FIG. 2, the image processing unit 140 may include an inverse volume rendering unit 141, a region of interest (ROI) setting unit 142, a position detecting unit 143 and a planar reformatting unit 144.

Figure 3:
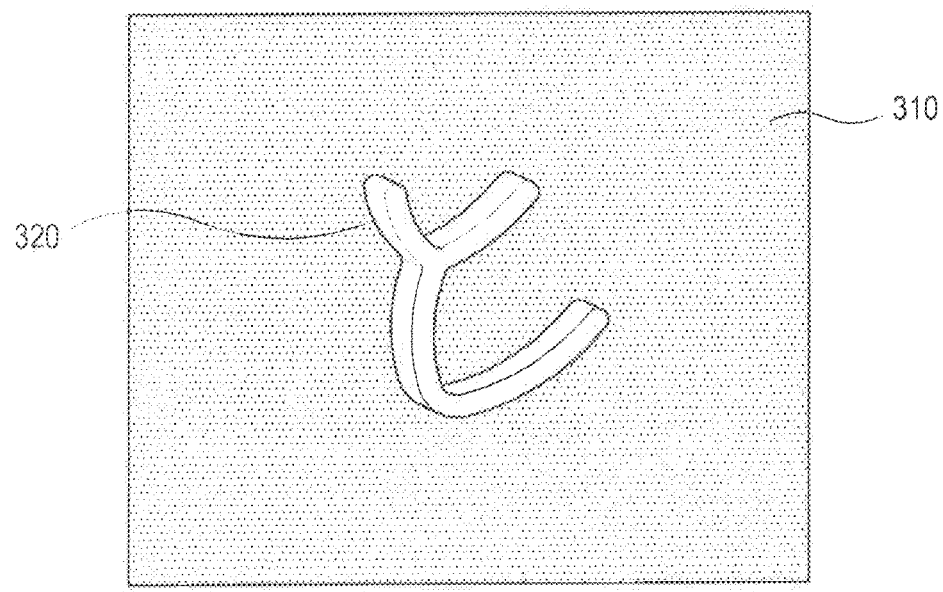
FIG. 3 shows an exemplary 3-dimensional reference image formed through inverse volume rendering in accordance with one embodiment of the present invention.
Figure 4:
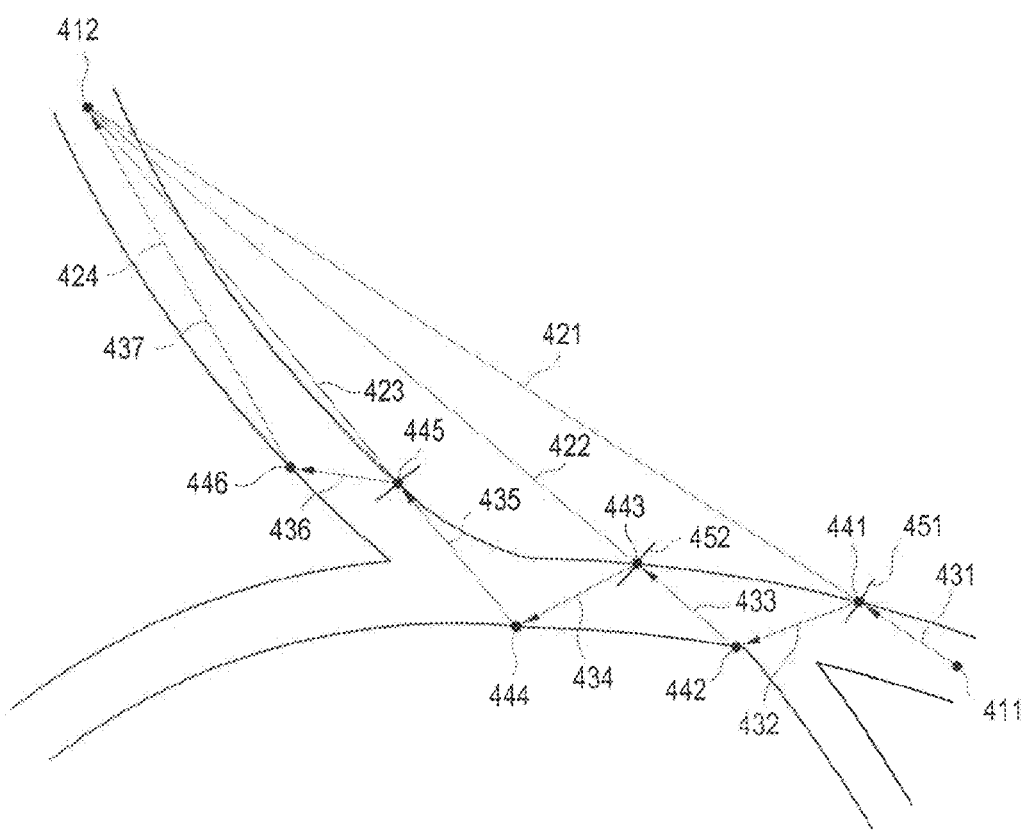
FIG. 4 is a schematic diagram showing a procedure of setting a region of interest in accordance with one embodiment of the present invention.

The inverse volume rendering unit 141 may be operable to perform inverse volume rendering upon the volume data by inverting gray levels of voxels contained in the volume data to thereby form a 3-dimensional reference image 310 containing the target object 320 of an un-echoic area, as shown in FIG. 3. The un-echoic area may be an area at which the ultrasound signals are not reflected, such as a blood vessel, pleural effusion, expansion of renal pelvis, hydrocephalic, urethra, duodenal atresia or the like.

From a user, the input unit 160 may receive setup information of ROI to be reformatted to the planar image from the 3-dimensional reference image. The setup information of ROI may include information of a start point and an end point of the ROI to be set on the target object of the un-echoic area in the 3-dimensional reference image 310. The ROI setting unit 142 may be operable to set the ROI based on the setup information of ROI. The ROI setting unit 142 may set the start point 411 and the end point 412 on the target object 320 based on the setup information of the ROI. The ROI setting unit 142 may set a first shortest line 421 connecting the start point 411 to the end point 412. The ROI setting unit 142 may detect a boundary point 441 along the first shortest line 421 from the start point 411 to the end point 412. It may set a first straight line 431 connecting the start point 411 to the detected boundary point 441. The boundary may be detected by using a change of brightness with a differential operator. In accordance with one embodiment of the present invention, the boundary may be detected by using an edge mask such as Sobel, Prewitt, Robert, Laplacian of Gaussian, Canny or the like. The ROI setting unit 142 may set a normal line 451 to the first straight line 431 at the boundary point 441. The normal line 451 may have a predetermined length. The ROI setting unit 142 may compute brightness values of voxels within a predetermined range along the normal line 451 from the boundary point 441 and determine a direction having a relatively larger mean brightness value. The ROI setting unit 142 may set a second straight line 432 from the first boundary point 441 toward the determined direction at a predetermined angle with respect to the first straight line 431. The ROI setting unit 142 may detect a boundary point 442 along the second straight line 432 and set a second shortest line 422 connecting the boundary point 442 to the end point 412. The ROI setting unit 142 may repeatedly perform the above procedure until the straight line extending straight from the boundary point is connected to the end point 412 without passing the boundary point. The ROI setting unit 142 may set the ROI of a curvature line shape to be reformatted to the planar image by using curve fitting with the start point 411, the end point 412 and a plurality of boundary points 441-446.

The user input unit 160 may further receive an instruction for rotating the 3-dimensional reference image 310. The instruction may include information upon a view point of the 3-dimensional reference image 310. The image processing unit 140 may be operable to rotate the 3-dimensional image to be displayed at a different view point in response to the instruction while the ROI set on the target object. Thus, the user may easily check whether or not the ROI is appropriately set along the target object.

The position detecting unit 143 may be operable to detect positions of voxels corresponding to the set ROI on the target object in the 3-dimensional reference image 310. The multi-planar reformatting unit 144 may be operable to detect data corresponding to the detected positions from the volume data, i.e., a gray level of brightness, and reformat the detected data to form planar image.

The storage unit 150 may be operable to store the volume data formed in the volume data forming unit 130. The display unit 170 may be operable to display the 3-dimensional reference image and the reformatted planar image.

As described above, since the present invention forms a 3-dimensional image containing a target object of an un-echoic area through the inverse volume rendering method and set the ROI along the target object to thereby reformat the planar image, stricture or atresia of the blood vessel may be easily observed.

In accordance with one embodiment of the present invention, there is provided an ultrasound system for forming an ultrasound image, comprising: a volume data acquiring unit operable to acquire volume data by transmitting/receiving ultrasound signals to/from a target object of an un-echoic area; and an image processing unit operable to perform inverse volume rendering upon the volume data to form a 3-dimensional image showing the target object and set a region of interest (ROI) on the target object in response to a user input, the image processing unit being configured to detect data corresponding to the ROI from the volume data and reformat the detected data to form a planar image.

In accordance with another embodiment of the present invention, there is provided a method of forming an ultrasound image, comprising: a) acquiring volume data by transmitting/receiving ultrasound signals to/from a target object of an un-echoic area; b) performing inverse volume rendering upon the volume data to form a 3-dimensional image showing the target object; c) setting a region of interest (ROI) on the target object in response to a user input; and d) reformatting data corresponding to the ROI in the volume data to form a planar image.

Any reference in this specification to "one embodiment," "an embodiment," "example embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system for forming an ultrasound image, comprising:
   a volume data acquiring unit configured to acquire volume data by transmitting/receiving ultrasound signals to/from a target object of an un-echoic area; and
   an image processing unit configured to perform inverse volume rendering upon the volume data to form a 3-dimensional image showing the target object; and
   a user input unit configured to receive a user input including setup information for setting a start point and an end point of the target object on the 3-dimensional image,
   wherein the image processing unit includes
   a ROI setting unit configured to set a first shortest line from the start point to the end point, automatically detect a first boundary point of the un-echoic area along the first shortest line for setting a first straight line from the start point to the first boundary point, detect a second boundary point in a direction of a predetermined angle from the first boundary point for setting a second straight line from the first boundary point to the second boundary point, set a second shortest line from the second boundary point to the end point, repeatedly perform the detection of boundary points and the setting of the straight lines and the shortest lines until the straight line is connected to the end point without passing through a boundary point, and set the ROI based on the start point, the end point, and the detected boundary points;
   a position detecting unit configured to detect positions of voxels corresponding to the ROI; and
   a reformatting unit configured to reformat data corresponding to the detected positions to the planar image with gray levels of brightness.

2. The ultrasound system of claim 1, wherein the volume data acquiring unit comprises:
   a transmit/receive unit configured to transmit the ultrasound signals to the target object and receive the ultrasound signals reflected from the target object to output reception signals; and
   a volume data forming unit configured to form the volume data of the target object based on the reception signals.

3. The ultrasound system of claim 1, wherein the imaging processing unit further comprises:
   an inverse volume rendering unit configured to perform the inverse volume rendering upon the volume data for inverting a gray level of brightness of each voxel contained in the volume data and forming the 3-dimensional image based on the inverted volume data.

4. The ultrasound system of claim 1, wherein the ROI setting unit sets a normal line at the boundary points and computes mean brightness of voxels along the normal line, the ROI setting unit being configured to set the straight line in a direction of relatively larger mean brightness.

5. The ultrasound system of claim 1, wherein the ROI setting unit sets the ROI of a curvature shape from the start point, the end point, and the boundary points through curve fitting.

6. A method of forming an ultrasound image, comprising:
   a) acquiring volume data by transmitting/receiving ultrasound signals to/from a target object of an un-echoic area;
   b) performing inverse volume rendering upon the volume data to form a 3-dimensional image showing the target object;
   c) receiving a user input including setup information for setting a start point and an end point of the target object on the 3-dimensional image;
   d) setting a region of interest (ROI) on the target object in response to a user input; and
   e) reformatting data corresponding to the ROI in the volume data to form a planar image,
   wherein the step d) includes
   d1) setting a first shortest line from the start point to the end point;
   d2) automatically detecting a first boundary point of the un-echoic area along the first shortest line for setting a first straight line from the start point to the first boundary point;
   d3) detecting a second boundary point in a direction of predetermined angle from the first boundary point for setting a second straight line from the first boundary point to the second boundary point;
   d4) setting a second shortest line from the second boundary point to the end point;
   d5) repeatedly performing the detection of boundary points and the setting of the straight lines and the shortest lines until the straight line is connected to the end point without passing a boundary point; and
   d6) setting the ROI based on the start point, the end point and the detected boundary points.

7. The method of claim 6, wherein the step a) includes:
   transmitting the ultrasound signals to the target object;
   receiving the ultrasound signals reflected from the target object to thereby output reception signals; and
   forming the volume data of the target object based on the reception signals.

8. The method of claim 6, wherein the inverse volume rendering is performed upon the volume data for inverting a gray level of brightness of each voxel contained in the volume data and forming the 3-dimensional image based on the inverted volume data, the ROI is set on the target object based on the setup information, and
   the step e) includes:
      detecting positions of voxels corresponding to the ROI; and
      reformatting the data corresponding to the detected positions to form the planar image with gray levels of brightness.

9. The method of claim 6, wherein the step d) further comprises:
   setting a normal line at the boundary points and computing a mean brightness of voxels along the normal line; and
   setting the straight line in a direction of relatively larger mean brightness.

10. The method of claim 6, wherein the ROI is set as a curvature shape from the start point, the end point, and the boundary points through curve fitting.

* * * * *